(12) United States Patent
Grez et al.

(10) Patent No.: US 7,699,552 B2
(45) Date of Patent: Apr. 20, 2010

(54) PUMP SYSTEM FOR A PERSONAL CARE APPLIANCE

(75) Inventors: Joseph W. Grez, North Bend, WA (US); Scott E. Hall, Issaquah, WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 404 days.

(21) Appl. No.: 10/539,699

(22) PCT Filed: Dec. 3, 2003

(86) PCT No.: PCT/IB03/05771

§ 371 (c)(1), (2), (4) Date: Jun. 16, 2005

(87) PCT Pub. No.: WO2004/054403

PCT Pub. Date: Jul. 1, 2004

(65) Prior Publication Data
US 2006/0289031 A1 Dec. 28, 2006

Related U.S. Application Data

(60) Provisional application No. 60/434,624, filed on Dec. 18, 2002.

(51) Int. Cl.
*B43K 5/04* (2006.01)

(52) U.S. Cl. .................................................. 401/155

(58) Field of Classification Search .................. 401/155, 401/161, 169, 171, 176, 179, 183–185
See application file for complete search history.

(56) References Cited

U.S. PATENT DOCUMENTS

| 818,000 | A | * | 4/1906 | Stevenson | 401/155 |
| 1,353,747 | A | * | 9/1920 | Harwood | 222/101 |
| 1,711,755 | A | | 5/1929 | Smith | |
| 4,270,672 | A | * | 6/1981 | Kraals | 222/95 |
| 4,826,341 | A | | 5/1989 | Kwak | |
| 6,325,076 | B1 | | 12/2001 | Ramirez | |

FOREIGN PATENT DOCUMENTS

| FR | 2290129 | 5/1976 |
| FR | 2748914 | 11/1997 |
| JP | 52165764 | 6/1951 |

* cited by examiner

Primary Examiner—Huyen Le

(57) ABSTRACT

A pump (10) for a personal care appliance which includes a flexible fluid cartridge member (12) having an exit opening (17) for the fluid at a forward end thereof (16), a base member (24) having a cutout portion (26) into which a fluid-filled portion (14) of the cartridge (24) can nest, and a pressing member (32) having a configuration which nests with the cutout portion over a substantial portion of its length, such that as the pressing member moves forwardly along its path, fluid in the fluid-filled portion is pressed out the exit opening and into a line connected to a workpiece element, such as a toothbrush brushhead.

17 Claims, 2 Drawing Sheets

US 7,699,552 B2

PUMP SYSTEM FOR A PERSONAL CARE APPLIANCE

CROSS REFERENCE TO RELATED APPLICATION

This application claims the benefit of U.S. provisional application Ser. No. 60/434,624 filed Dec. 18, 2002, which is incorporated herein by reference.

This invention relates generally to pump systems for personal care devices, and more specifically concerns such a system which includes a fluid-containing cartridge member and a roller or pressing member for moving fluid from the cartridge member into a fluid line leading to the workpiece.

It is well known for certain personal care devices, such as, for instance, toothbrushes and shavers, as well as other such appliances, to include a system for dispensing a fluid during operation of the appliance, which may assist in the function or efficacy of the personal care device. Many of these fluid-dispensing appliances include a pump, which actively moves the fluid from a cartridge member/reservoir to a workpiece portion of the appliance, e.g. a toothbrush brushhead.

One type of pump which is used in such a device is a peristaltic pump, i.e. a pump which includes a pressing or contact member, such as, for instance, a roller, which in operation presses upon a fluid-containing cartridge in such a manner as to force fluid therein to an exit point in a forward end of the cartridge, without the pressing member, e.g. roller, coming into contact with the fluid. Peristaltic pumps can be advantageous for several reasons, including the possibility of maintaining sterility of the fluid. In some cases, peristaltic pumps are precharged, so that as the pressing member forces fluid out of the forward end (pump chamber portion) of a cartridge, fluid from a reservoir portion of the cartridge flows in behind the pressing member as it moves toward the exit point of the cartridge, so that upon completion of one dispensing event of fluid, a pump chamber portion of the cartridge is filled and ready for another dispensing action.

However, in practice there are several difficulties with a precharged peristaltic pump. As the pressing member moves along the cartridge, wrinkles develop in the cartridge material as the pressing member flattens the cartridge. Although the cartridge material is flexible, the cross-sectional circumference of the cartridge remains constant as well as the width of the cartridge in the pump chamber area. With the width being constant, the cartridge material must fold when the cartridge is compressed against conventional flat surfaces.

The resulting wrinkles can result in weaknesses in the cartridge material; eventually a break or leak in the cartridge wall can occur, leading to failure of the cartridge. Further, existing peristaltic pumps are often inefficient, with substantially less than all the fluid in the cartridge being dispensed. In addition, the pumping rate of fluid from such devices can vary during operation, which is undesirable.

It would thus be desirable to have a peristaltic-type pump, where there is no contact between the pressing member and the fluid as it is dispensed, in which the pump rate is consistent with little or no wrinkles developing in the cartridge member as the pressing member moves through its path of travel over the cartridge member, dispensing fluid therefrom.

Accordingly, the present invention is a pump system for a personal care appliance, comprising: a fluid cartridge member made of flexible material, the fluid cartridge member having a fluid-filled portion and an exit opening for the fluid in the cartridge for delivery to a line which connects to a workpiece portion of the appliance; a base member having a cutout portion into which the fluid-filled portion of the cartridge member can nest; and a pressing member, wherein at least a nesting portion of which has a configuration which substantially matches the cross-section contact portion of the base member, such that, over at least a substantial portion of the length of the cutout portion, the fluid-filled portion and the pressing member substantially nest with the contact portion, so that as the pressing member is moved in operation forwardly over the cartridge, fluid is moved from the fluid-filled portion through the exit opening, with the flexible cartridge being flattened during such action substantially without creasing of the cartridge.

Figure 1:
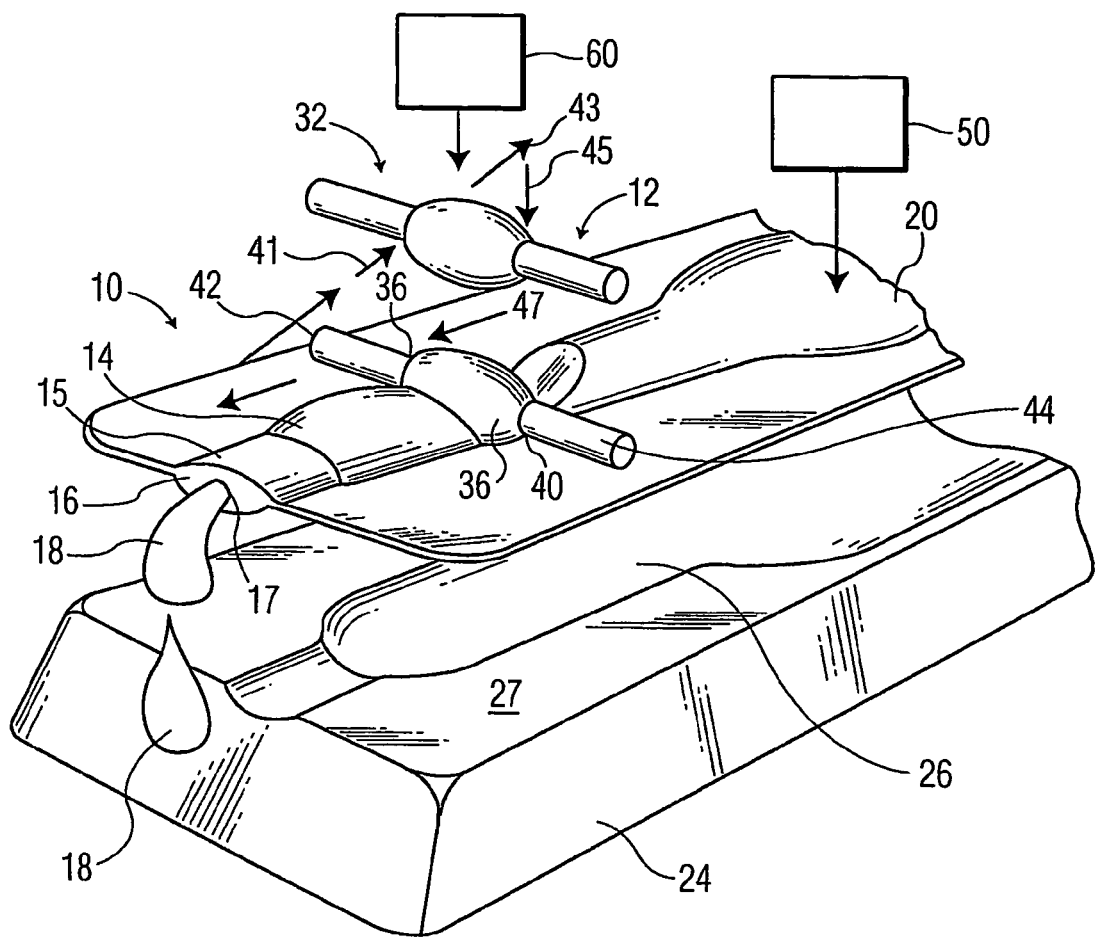
FIG. 1 is a perspective view of the improved pump of the present invention.

Referring to FIG. 1, the present invention is an improved pump system, which is useful for dispensing fluid in certain personal care appliances, and is referred to generally at 10. Personal care appliances, for instance, include a toothbrush, in particular a power toothbrush, in which a dentifrice or oral medication is applied to the brushhead for use in the oral cavity (specifically the teeth or the gums), or an electric shaver in which a fluid is dispensed in the vicinity of the contact between the shaver and the skin to make the shaving process more comfortable. Other similar personal care appliances, particularly relating to skin care, are known, in which a fluid is applied to the area of interest in the vicinity of the workpiece.

Referring to FIG. 1, a fluid-containing cartridge member is shown generally at 12. Cartridge member 12 is made of flexible material, such as a flexible plastic or other similar material, and includes a hollow area therein, in which fluid is present, referred to generally at 14. In the embodiment shown, the fluid-filled portion 14, which can also be referred to as a pump chamber, is shown to be elongated and can be of varying dimensions. In the embodiment shown, fluid-filled portion 14 is approximately 1 inch long, 0.5 inches wide, and approximately 0.5 inch high at its highest (filled) dimension, while the entire cartridge is 3 inches long by 1.5 inches wide. Since the cartridge member 12 is made of flexible material, the fluid-filled portion 14 in cross-section tends to be somewhat oval-like, gradually increasing in dimension from the two longitudinal edges to a centerline of greatest dimension.

The fluid-filled portion in the embodiment shown has an exit neck portion 15, which is narrower than the remainder of the fluid-filled portion. At the forward end 16 of neck portion 15 is an exit opening 17 from which fluid 18 is dispensed in normal pump action.

Figure 4:
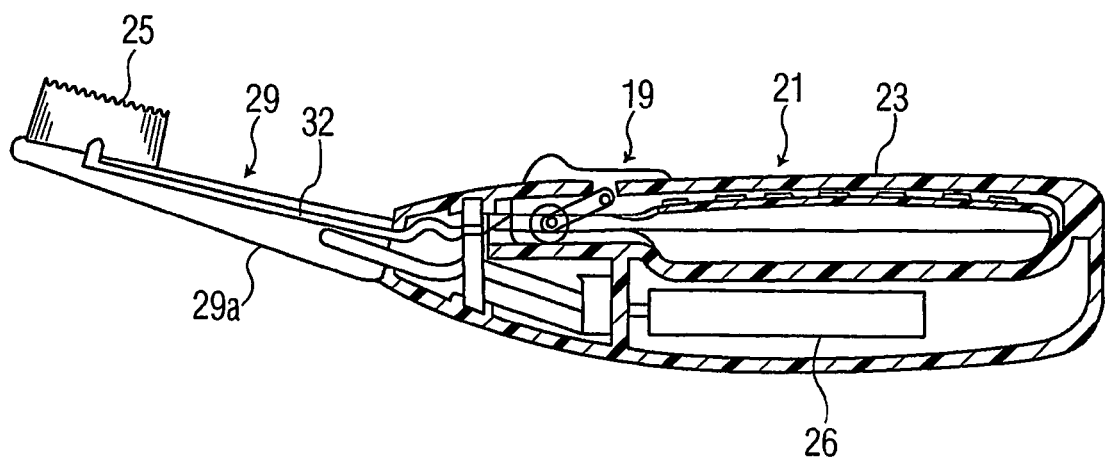
FIG. 4 is a cross-sectional view showing a power toothbrush with the improved pump of the present invention.

Referring briefly to FIG. 4, which shows a pump 19 in a power toothbrush 21, a fluid tube 32 receives fluid from opening 17 and extends up to a brushhead 25. The toothbrush includes a handle portion 23, which includes a driving system 26 for the toothbrush and a driven member assembly 29.

In the embodiment of FIG. 1, exit opening 17 is circular or oval-shaped, approximately 0.1 inches at its greatest diameter. In the toothbrush application, the tube will extend up through a mounting arm 29a of the toothbrush and into the brushhead 25 mounted on the end of arm 29a. In other appliances, there will also be a connecting line of some kind between the exit opening 17 and the workpiece or working portion of the appliance. In the embodiment shown (FIG. 1), fluid-filled portion 14 is shown in fluid communication within the cartridge 12 with a larger fluid reservoir 20 to the rear of fluid-filled portion 14. However, it is not essential in the present invention that the fluid cartridge includes a fluid reservoir.

Although FIG. 1 shows a cartridge 12 in which fluid-filled portion 14 covers substantially less than the entire area of cartridge 12, it should be understood that the fluid-filled portion 14 could cover a greater portion of the cartridge than shown and in some cases could extend for the entire width of the cartridge. Also, neck portion 15 is not necessary, although it can increase the efficiency and the consistency of the dispensing of the fluid. Fluid opening 17 will usually be relatively small.

A second portion of the pump system 10 is a base or anvil member 24. Base member 24 is made from a rigid, relatively non-resilient material, such as a hard plastic or closed-cell foam, and has a cutout or trough portion 26 which is configured to match the configuration of the lower portion of the fluid-filled port 14, such that the fluid-filled portion nests within cutout portion 26. The embodiment of FIG. 1 shows that the fluid-filled portion 14 fits within the cutout portion while the remainder of the cartridge fits against upper surface 27 of base member 24. However, the entire cartridge, with the fluid-filled portion extending from edge to edge, could alternately be configured to fit within a matching cutout portion 26. The important characteristic is that the fluid-filled portion 26 nest within the cutout portion of the base member.

The third portion of the pump system 10 is the pressing member 32, which in some cases is a rolling member if in pump operation it is to roll along the length of fluid-filled portion 14. The pressing member 32 is mounted so that upon forward movement thereof, either rolling or sliding, by hand (manual) or by a motor (power), fluid in the fluid-filled portion/pumping chamber 14 is pressured and moved forwardly out of exit opening 17. Pressing member 32 includes a nesting portion 36.

In the embodiment shown, nesting portion 36 has a length which is approximately the width of the fluid-filled portion 14 of cartridge 12, and the width of cutout portion 26 of base member 24. Its configuration, from end to end, is such that it can nest within cutout portion 26, i.e. it curves from end to end to match the curve of the cutout portion 26, as well as the curve of the fluid-filled portion 14 of the cartridge.

The nesting portion is so curved (from end to end) over at least a portion (but not necessarily all) of its circumference. In the case where the pressing member 32 rolls over the fluid-filled portion, the curved configuration is present over the entire circumference of the nesting portion, as shown in FIG. 1, while if the pressure member is to slide over the fluid-filled portion, only a relatively small part of the circumference of the nesting portion is required to have such a configuration. The diameter of the nesting portion increases from its respective ends toward the center thereof in such a manner that it has basically the same configuration as cutout portion 26.

Extending from ends 38 and 40 of the nesting portion 36 are mounting elements 42 and 44, which, in the embodiment shown, are elongated rods. In operation, mounting elements 42 and 44 are pushed or rotated forwardly over the length of the fluid-filled portion, either by a hand-assisted mechanical device, such as a thumb activated lever, or by a power element, such as a motor. FIG. 4 shows a thumb-activated member. Movement of the mounting elements 42 and 44 in the direction of the exit opening 17 gradually squeezes or presses the fluid present between exit opening 17 and the pressing member 32 out of the fluid-filled portion 14 (pump chamber) at the exit opening.

Having a base portion 24 with a cutout portion 26 in which the fluid-filled portion 14 (pump chamber) and the pressing member both nest results in an efficient, clean pressing of fluid out of the pumping chamber without wrinkling or creasing the fluid cartridge material. The pressuring force is supplied by a spring 60 or other pressure means, or the pressing member could ride in a track positioned to produce the required pressure. Such an arrangement overcomes the disadvantages of the prior art discussed above.

In use, the fluid-filled portion 14 of a cartridge is placed into the cutout portion of base portion 24. The pressing element 32 is then used to deform the fluid-filled portion 14 and move fluid out of the fluid-filled portion. The pressing member however is shaped to maintain the constant cross-sectional circumference of the fluid-filled portion as it moves along the fluid-filled portion, preventing wrinkling of the material.

When the pressing member 32 reaches the forward end of its path, in the vicinity of exit opening 17, at the forward end of the cartridge member, the pressing member 32 is lifted up and returned to its starting point at the rear of the fluid-filled portion/pumping chamber. In FIG. 1, this is shown by the pressing member moving rearwardly along an inclined path indicated at 41 to rear point 43, and then downwardly at 45 to again engage the fluid-filled portion 14 of the cartridge. A more detailed explanation is provided relative to FIG. 3 below.

The fluid-filled portion/pumping chamber 14 can be refilled in various ways. In one approach, the material comprising cartridge member is sufficiently stiff that it will rebound to its original curved configuration to the rear 47 of the pressing member 32 as the pressing member moves forwardly. Fluid from the reservoir will be drawn into the pumping chamber 14 by vacuum action. This maintains fluid in the chamber as the pressing member 32 moves along its path. In another arrangement, a pressure member, such as a spring, shown at 50, can be used to maintain a selected amount of pressure on the reservoir 20, moving fluid into chamber 14 behind the roller, as the roller moves forwardly over the fluid-filled portion 14, refilling that portion with fluid.

Figure 2:
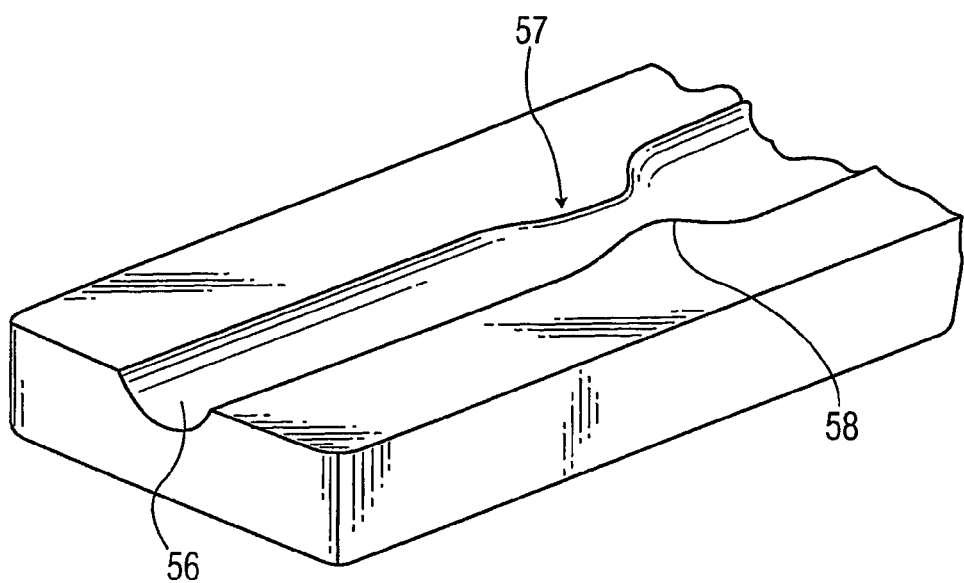
FIG. 2 is a perspective view of a variation of the base portion of the pump, having a tapered configuration.

In a variation of the above arrangement, referring to FIG. 2, the trough or cutout portion 56 is made narrower at tapered portion 57 than the length of pressing member 32 at the beginning point 58 of the path of the pressing member, so that the pressing member has a relatively small contact with the fluid-filled portion of the cartridge, since the nesting portion can't nest in the trough. The trough widens quickly, however, to the length of the nesting portion of the pressing member, so that the nesting portion can nest against the fluid-filled portion of the cartridge in the cutout portion of the base member. A spring or track arrangement also provides the required pressing force, as in the embodiment of FIG. 1. This arrangement results in a gradual increase in the pumping pressure or force on the fluid-filled portion until the cutout portion 56 reaches its full width, at which point fluid moved from the fluid-filled portion to the fluid line reaches its maximum rate.

Figure 3:
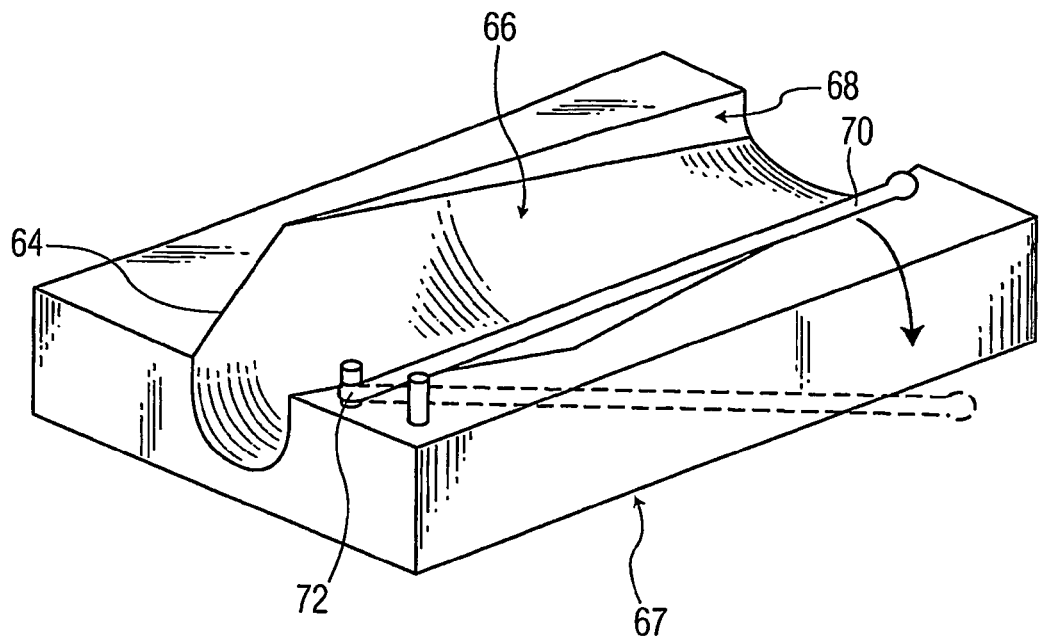
FIG. 3 is a perspective view of another embodiment of the base portion of the pump, which includes a return arm for the pressing member.

FIG. 3 shows a further embodiment of the present invention, in which a forward portion 64 of cutout portion 66 of base member 67 is tapered inwardly. This can be either a separate feature of cutout portion 66 or in addition to an outward tapered portion 68 in the first part of the cutout portion, as discussed above with respect to FIG. 2. As the pressing member moves along its path in this embodiment, the pressing member will first gradually engage the fluid-filled portion in the cutout portion, to the point where it is fully engaged and completely nested with the cutout portion. Further along the path, the pressing member is gradually lifted upwardly out of contact with the cutout portion and the fluid-filled portion of the cartridge by the inward taper 64 of the trough. In the embodiment shown, the tapered portion 64 results in the pressing member being more elevated at the end of its path relative to the base portion than its position at the beginning thereof.

When the pressing member reaches its most forward and hence its most elevated position, a return arm 70 is swung into position by a compression spring 72 alongside the cutout portion, and the pressing member is returned to its start position by a return spring (not shown). At its start position, the arm 70 is again moved outwardly by spring force away from the pressing member. Hence, there is a back-and-forth action of arm 70 controlled by various springs, which results in the pressing member moving back to its start position, ready for another dispensing action.

Hence, a pump system has been described for use in a personal care appliance. The pump is arranged for a peristaltic action, with a flexible fluid cartridge. The system includes a cutout portion in a base member and a similarly configured pressing member, to press fluid out of the fluid-filled portion of the cartridge, which nests in the cutout portion, without wrinkling the cartridge and in an even, consistent manner.

Although a preferred embodiment of the invention has been described for purposes of illustration, it should be understood that various changes, modification and substitutions may be incorporated in the embodiment without departing from the spirit of the invention, which is defined by the claims which follow.

The invention claimed is:

1. A pump system for a personal care appliance, comprising:
   a fluid cartridge member having a flexible fluid-filled portion and an exit opening for the fluid in the cartridge, for delivery to a line which connects to a workpiece portion of the appliance;
   a base member having a cutout portion into which the fluid-filled portion of the cartridge member can nest; and
   a pressing member, at least a nesting portion of which has a length and diameter which substantially match the cross-section of the cutout portion of the base member for at least a substantial portion of the length of the cutout portion, wherein the nesting portion of the pressing member directly contacts the fluid-filled portion substantially entirely across the cutout portion, wherein the pressing member includes two mounting elements which extend outwardly away from the cutout portion and outwardly from the opposing ends of the nesting portion sufficiently that the pressing member is movable by user action on the mounting elements, so that as the pressing member is moved in operation forwardly over the cartridge, fluid is moved from the fluid-filled portion through the exit opening, with the flexible cartridge portion being flattened during such action substantially without creasing of the cartridge, wherein an end part of cutout portion tapers inwardly such that as the pressing member moves along its path, it is lifted upwardly from the base member out of nesting contact with the cutout portion.

2. The system of claim 1, wherein the nesting portion of the pressing member is configured to nest with the cutout portion around its entire circumference, permitting the nesting portion to roll along the fluid-filled portion of the cartridge, pressing fluid out therefrom through the exit opening.

3. The system of claim 1, wherein a beginning part of the cutout portion is narrower than the length of the nesting portion of the pressing means but tapers outwardly to a point where the nesting portion fully nests within the cutout portion.

4. A pump system for a personal care appliance, comprising:
   a fluid cartridge member made of flexible material, the fluid cartridge member having a fluid-filled portion and an exit opening for the fluid in the cartridge, for delivery to a line which connects to a workpiece portion of the appliance;
   a base member having a cutout portion into which the fluid-filled portion of the cartridge member can nest; and
   a pressing member, at least a nesting portion of which has a configuration which substantially matches the cross-section of the cutout portion of the base member, such that, over at least a substantial portion of the length of the cutout portion, the fluid-filled portion and the pressing member can substantially nest with the cutout portion, so that as the pressing member is moved in operation forwardly over the cartridge, fluid is moved from the fluid-filled portion through the exit opening, with the flexible cartridge being flattened during such action substantially without creasing of the cartridge,
   wherein the fluid cartridge includes a reservoir portion from which fluid moves to replenish fluid in the fluid-filled portion after a dispensing action.

5. The system of claim 4, wherein the fluid-filled portion comprises a material which inflates after being compressed by the pressing member, such that fluid from the reservoir moves into the empty part of the fluid-filled portion by vacuum action.

6. The system of claim 4, including means for pressuring the reservoir so that fluid is moved into the emptied part of the fluid-filled portion behind the pressing member as the pressing member moves along its path.

7. The system of claim 4, wherein a beginning part of the cutout portion is narrower than the length of the nesting portion of the pressing member but tapers outwardly to a point where the nesting portion fully nests within the cutout portion.

8. The system of claim 4, wherein an end part of the cutout portion tapers inwardly such that as the pressing member moves along its path, it is lifted upwardly from the base member and out of nesting contact with the cutout portion.

9. A power toothbrush, comprising:
   a handle portion having a driving system and a power supply for the driving system;
   a driven member assembly having an arm on which a brushhead is mounted and a structural element for connecting the driven member assembly to the driving system;
   a pump system for dispensing fluid to the brushhead, the pump assembly including a fluid cartridge member made of flexible material, the fluid cartridge member having a flexible fluid-filled portion and an exit gap for the fluid in the cartridge, for delivery to a line which connects the pump to the brushhead;
   a base member having a cutout portion into which the fluid-filled portion of the cartridge member can nest; and
   a pressing member, at least a nesting portion of which has a length and a diameter which substantially match the cross-section of the cutout portion of the base member for at least a substantial portion of the length of the cutout portion, wherein the nesting portion directly contacts the fluid-filled portion, so that as the pressing member is moved in operation over the cartridge, fluid is moved from the fluid-filled portion through the exit opening into the connecting line, with the flexible cartridge being flattened during such action substantially without creasing thereof.

10. The toothbrush of claim 9, wherein the pressing member includes two mounting elements which extend outwardly from opposing ends of the nesting portion, sufficiently that the pressing member is movable by action on the mounting elements.

11. The toothbrush of claim 9, wherein the nesting portion is configured to nest with the cutout portion around its entire circumference, permitting the nesting portion to roll along the fluid-filled portion of the cartridge, pressing fluid out therefrom through the exit opening.

12. The toothbrush of claim 9, including means for pressurizing the reservoir so that fluid is moved into the emptied part of the fluid-filled portion behind the pressing member as the pressing member moves along its path.

13. The toothbrush of claim 9, wherein the fluid cartridge includes a reservoir portion from which fluid moves to replenish fluid in the fluid-filled portion after a dispensing action.

14. The toothbrush of claim 9, wherein a beginning part of the cutout portion is narrower than the length of the nesting portion of the pressing member but tapers outwardly to a point where the nesting portion hilly nests within the cutout portion.

15. The toothbrush of claim 9, wherein an end part of the cutout portion tapers inwardly such that as the pressing member moves along its path, it is lifted upwardly from the base member and out of nesting contact with the cutout portion.

16. A pump system for a personal care appliance, comprising:

a fluid cartridge member having a flexible fluid-filled portion and an exit opening for the fluid in the cartridge, for delivery to a line which connects to a workpiece portion of the appliance;

a base member having a cutout portion into which the fluid-filled portion of the cartridge member can nest; and a pressing member, at least a nesting portion of which has a length and diameter which substantially match the cross-section of the cutout portion of the base member for at least a substantial portion of the length of the cutout portion, wherein the nesting portion of the pressing member directly contacts the fluid-filled portion substantially entirety across the cutout portion, wherein the pressing member includes two mounting elements which extend outwardly away from the cutout portion and outwardly from the opposing ends of the nesting portion sufficiently that the pressing member is movable by user action on the mounting elements, so that as the nesting member is moved in operation forwardly over the cartridge, fluid is moved from the fluid-filled portion through the exit opening, with the flexible cartridge portion being flattened during such action substantially without creasing of the cartridge, wherein the pump system includes a support arm which is arranged and operative to support the pressing member for return of the pressing member to a start point of its pressing action.

17. The system of claim 16, wherein return of the pressing member is by spring action.

* * * * *